United States Patent
Wang et al.

(10) Patent No.: US 11,014,914 B2
(45) Date of Patent: *May 25, 2021

(54) OPIOID RECEPTOR (MOR) AGONIST SALT, FUMARATE SALT CRYSTAL FORM I THEREOF AND PREPARATION METHOD THEREOF

(71) Applicant: Jiangsu Hengrui Medicine Co., Ltd., Jiangsu (CN)

(72) Inventors: Lin Wang, Jiangsu (CN); Likun Wang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/499,453

(22) PCT Filed: Apr. 13, 2018

(86) PCT No.: PCT/CN2018/082935
§ 371 (c)(1),
(2) Date: Sep. 30, 2019

(87) PCT Pub. No.: WO2018/188643
PCT Pub. Date: Oct. 18, 2018

(65) Prior Publication Data
US 2020/0048229 A1   Feb. 13, 2020

(30) Foreign Application Priority Data

Apr. 14, 2017  (CN) .................. 201710242119.3

(51) Int. Cl.
*C07D 405/04*   (2006.01)
(52) U.S. Cl.
CPC ........ *C07D 405/04* (2013.01); *C07B 2200/13* (2013.01)
(58) Field of Classification Search
CPC .................................................. C07D 405/04
USPC ...................................................... 546/280.1
See application file for complete search history.

(56) References Cited

U.S. PATENT DOCUMENTS 10,442,793 B2 * 10/2019 Li .................. C07D 405/04
2018/0297988 A1   10/2018 Li et al.

FOREIGN PATENT DOCUMENTS

| CA | 3000761 A1 | 4/2017 |
| CN | 103702561 A | 4/2014 |
| WO | 2012129495 A1 | 9/2012 |
| WO | 2017063509 A1 | 4/2017 |

OTHER PUBLICATIONS

Thackaberry Expert Opin. Drug Metab. Toxicol. (2012) 8(11):1419-1433.*
Liang et al., "Efficient Diastereoselective Intermolecular Rhodium-Catalyzed C—H Amination", Angewandte Chemie, 45(28), pp. 4641-4644, 2006.
Chen et al., "Structure-Activity Relationships and Discovery of a G Protein Biased Opioid Receptor Ligand, [(3-Methoxythiophen-2-yl) methyl] [{2-[(9R)-9-(pyridin-2-yl)-6-oxaspiro-[4.5]decan-9-yl]ethyl}) amine (TRV130), for the Treatment of Acute Severe Pain", Journal of Medicinal Chemistry, 56, pp. 8019-8031, 2013.
SM et al., "A G protein-biased ligand at the m-opioid receptor is potently analegesic with reduced gastronitestinal and respiratory dysfuntion compared with morphine", J. Pharmocol Exp Ther. 344(3), pp. 708-717, 2013 (Abstract Only).
Fichna et al., The Endomorphin System and Its Evolving Neurophysiological Role, Pharmacological Reviews, 59, pp. 88-123, 2007.
Int'l Written Opinion of the International Searching Authority dated Jul. 18, 2018, in Int'l Application No. PCT/CN2018/082935.
Int'l Search Report dated Jul. 18, 2018 in Int'l Application No. PCT/CN2018/082935.

* cited by examiner

*Primary Examiner* — Nizal S Chandrakumar
(74) *Attorney, Agent, or Firm* — Ice Miller LLP

(57) ABSTRACT

Relating to an opioid receptor agonist (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine fumarate salt, a fumarate salt crystal form I thereof, and a preparation method and an application therefor.

11 Claims, 3 Drawing Sheets

(I)

OPIOID RECEPTOR (MOR) AGONIST SALT, FUMARATE SALT CRYSTAL FORM I THEREOF AND PREPARATION METHOD THEREOF

CROSS-REFERENCE TO RELATED APPLICATIONS

This application is a Section 371 of International Application No. PCT/CN2018/082935, filed Apr. 13, 2018, which was published in the Chinese language on Oct. 18, 2018, under International Publication No. WO 2018/188643 A1, which claims priority under 35 U.S.C. § 119(b) to Chinese Application No. 201710242119.3, filed Apr. 14, 2017, the disclosures of which are incorporated herein by reference in their entireties.

FIELD OF INVENTION

The present invention relates to (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine salt, a fumarate salt crystal form I thereof and a preparation method thereof, use of the salt and the fumarate salt crystal form I in pharmaceutical composition and use of said salt, fumarate salt crystal form I and the composition in manufacturing a medicament for treating and/or preventing opioid receptor (MOR) agonist-related diseases.

PRIOR ARTS

Opioid receptors are an important class of G protein-coupled receptors (GPCRs), which are targets for the binding of endogenous opioid peptides and opioid drugs. The activated opioid receptors have a regulatory effect on nervous system immunity and the endocrine system, and opioid drugs are the strongest and commonly used central analgesics. Endogenous opioid peptides are naturally generated opioid active substances in mammals, and currently known endogenous opioid peptides are broadly classified into enkephalins, endorphins, dynorphins and neoendorphins (Pharmacol Rev 2007; 59: 88-123). There are corresponding opioid receptors in the central nervous system, namely μ (MOR), δ (DOR), κ (KOR) receptors and the like. MOR is a target for endogenous enkephalins and opioid analgesics such as morphine.

Long-term use of opioid drugs may produce tolerance and side effects such as respiratory depression and constipation, and these side effects have been shown to be closely related to the function of β-arrestin. In order to reduce the side effects of opioids, drugs can be designed based on the negative β-arrestin biased ligand of MOR, which can reduce the side effects mediated by β-arrestin and enhance the therapeutic effect. In a study of oxaspiro derivatives of the present invention acting as a MOR selective drug, Trevenalnc company found that aryl substitution at the benzyl position is less active (J. Med. Chem. 2013, 56, 8019-8031). However, WO2017063509 (Patent Application No. PCT/CN2016/101064, filling date 30 Sep. 2016) disclosed a MOR compound which exhibits high activity, significantly increased Emax, significantly improved hERG and single configuration after aryl cyclization at the benzyl position, the structure of which is represented by formula (II):

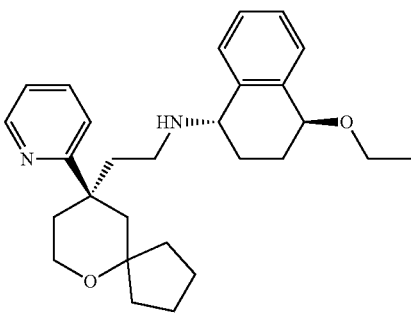

Since the solubility of the compound represented by formula (II) is low, in order to further improve the solubility of the compound, we have carried out salt formation studies on the compound represented by formula (II), and the acids investigated include fumaric acid. At present, there's no report of the salt of the compound represented by the formula (II) or crystal form thereof, and it is well known that the structure of crystal acting as pharmaceutically active ingredient often affects the chemical and physical stability of the drug, and the difference in crystallization conditions and storage conditions may result in a change of the crystal structure of a compound, sometimes also accompanied by the formation of other forms of crystal form. In general, amorphous pharmaceutical products have no regular crystal structure and often have other defects, such as poor product stability, difficulty in filtration, easy agglomeration, and poor fluidity. Therefore, it is necessary to improve various aspects of the above products.

Content of the Present Invention

The technical problem to be solved in the present invention is to provide a fumarate salt of (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine (represented by formula (I)), a crystal form I thereof and a preparation method thereof. The salt possesses good solubility and the crystal form possesses good stability.

The technical solutions of the present invention are as follows:

The present invention provides a (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine fumarate salt of the compound represented by formula (II),

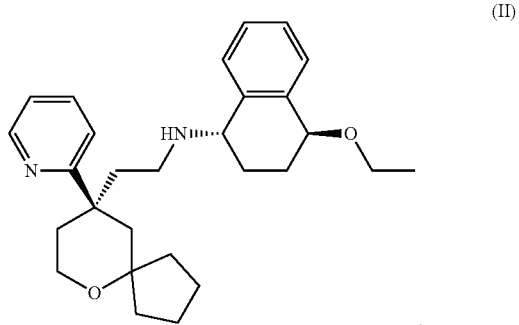 [SMILES: CCO[C@H]1CC[C@H](NCC[C@@]2(c3ccccn3)CCOC3(CCCC3)C2)c2ccccc21]

In one embodiment, the chemical ratio between (1S,4S)-4-ethoxy-N-(2-((R)-9-(pyridin-2-yl)-6-oxaspiro[4.5]deca-9- yl)ethyl)-1,2,3,4-tetrahydronaphthalen-1-amine and fumaric acid is 1:1, the structure thereof is represented by formula (I)

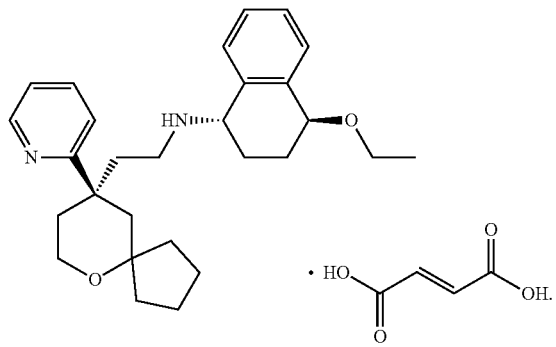

The present invention also provides the preparation method of the salt, wherein, the method comprises the step of reacting (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine with fumaric acid.

In one embodiment, the salt formation is carried out in a solvent, wherein said solvent is selected from alcohols, ethers and esters, and said alcohol solvent is preferably methanol, ethanol or isopropanol, and said ether is preferably diethyl ether, methyl tert-butyl ether, tetrahydrofuran or dioxane, and said ester solvent is selected from ethyl acetate, isopropyl acetate and butyl acetate.

In another embodiment, said reaction temperature is 10-80° C.

The present invention further provides crystal form I of the compound represented by formula (I), wherein: the X-ray powder diffraction pattern represented by diffraction angle 2θ obtained by Cu-Kα radiation shows characteristic peaks at diffraction angles 2θ of 5.76, 10.82, 11.47, 12.69, 13.86, 14.77, 15.27, 15.74, 17.26, 17.61, 18.34, 22.39, 23.06, 23.75 and 24.23, wherein the error range for each of the characteristic peaks 2θ is ±0.2.

In one embodiment, characteristic peaks appeared at diffraction angles 2θ of 5.76, 10.82, 11.47, 12.69, 13.86, 14.77, 15.27, 15.74, 17.26, 17.61, 18.34, 19.27, 19.94, 20.37, 21.42, 21.73, 22.02, 22.39, 23.06, 23.75, 24.23 and 24.73, wherein the error range for each of the characteristic peaks 2θ is ±0.2.

In another embodiment, characteristic peaks appeared at diffraction angles 2θ of 5.76, 7.86, 10.82, 11.47, 12.28, 12.69, 13.86, 14.77, 15.27, 15.74, 16.26, 17.26, 17.61, 18.34, 19.27, 19.94, 20.37, 21.42, 21.42, 21.73, 22.02, 22.39, 23.06, 23.75, 24.23, 24.73, 25.54, 26.68, 28.59, 29.48, 31.04, 32.90 and 35.73, wherein the error range for each of the characteristic peaks 2θ is ±0.2.

The present invention also provides a method for preparing crystal form I, wherein said method is selected from (i) Dissolving the compound represented by formula (I) in a solvent, crystallizing, filtering, and drying to obtain the target crystal form I; the solvent is preferably an ether solvent, more preferably tetrahydrofuran;

(ii) Adding the compound represented by formula (I) into a solvent, triturating, filtering, and drying to obtain the target crystal form I; the solvent is selected from ethers, ketones, esters and nitriles; the ether solvent is selected from tetrahydrofuran, dioxane, diethyl ether and methyl tert-butyl ether; the ketone solvent is selected from acetone, acetophenone, methyl isobutyl ketone and methyl pyrrolidone; the ester solvent is selected from ethyl acetate, isopropyl acetate and butyl acetate, and the nitrile solvent is selected from acetonitrile and propionitrile.

The present invention further relates to a pharmaceutical composition of the compound represented by formula (I), or crystal form I thereof, comprising one or more pharmaceutically acceptable carriers, diluents or excipients.

The present invention further relates to a use of the compound represented by formula (I), crystal form I thereof, or the pharmaceutical composition in manufacturing a medicament for treating related diseases mediated by an opioid receptor (MOR) agonist.

The related diseases mediated by an MOR receptor agonist of the present invention are selected from the group consisting of pain, immune dysfunction, inflammation, esophageal reflux, neurological and psychiatric diseases, urinary and reproductive diseases, cardiovascular diseases, and respiratory diseases, preferably pain.

The present invention further provides a use of the compound represented by formula (I), crystal form I thereof, the pharmaceutical composition of the compound represented by formula (I), and the pharmaceutical composition of crystal form I in manufacturing a medicament for preventing or treating pain and pain related diseases.

The pain of the present invention is selected from postoperative pain, pain caused by cancer, neuropathic pain, traumatic pain and pain caused by inflammation.

The cancer of the present invention is selected from the group consisting of breast cancer, endometrial cancer, cervical cancer, skin cancer, prostate cancer, ovarian cancer, fallopian tube tumor, ovarian tumor, hemophilia, and leukemia.

The present invention further provides a use of the compound represented by formula (I), crystal form I thereof, the pharmaceutical composition of the compound represented by formula (I), and the pharmaceutical composition of crystal form I in manufacturing a medicament for agonizing or antagonizing MOR receptor.

The structural measurement and crystal form study of the obtained crystal form I of the compound represented by formula (I) are conducted by using X-ray powder diffraction pattern (XRPD), differential scanning calorimetry (DSC), or thermogravimetric analyzer (TGA).

The recrystallizing method used for crystal form I is not particularly limited and can be carried out by using a common recrystallization operation method. For example, dissolving the compound represented by formula (I) in an organic solvent and then crystallizing by adding into an anti-solvent, after the crystallization is completed, filtering and drying to obtain a desired crystal.

The crystallization method of the present invention includes evaporation crystallization, ambient crystallization, cooling crystallization, seed-induced crystallization, and the like.

In the preparation method for the crystal form of the present invention, any form of the compound represented by formula (I) may be used as the starting material, and specific form includes but is not limited to: amorphous, any crystal form and the like.

In the description and claims of the present application, unless otherwise indicated, the scientific and technical terms used herein have the meanings commonly understood by those skilled in the art. However, for a better understanding of the present invention, definitions and explanations of some related terms are provided below. In addition, when definitions and explanations of the terms provided by the present invention are inconsistent with the meanings generally understood by those skilled in the art, the definitions and explanations of the terms provided by the present application shall prevail.

The term "$C_{1-6}$ alkyl" in the present invention represents a linear or branched alkyl group having 1 to 6 carbon atoms, and specific examples include, but are not limited to, methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, and the like.

The term "hydroxyl group" used in the present invention represents —OH group and the like.

The term "cyano group" used in the present invention represents —CN group and the like.

The term "ketone solvent" used in the present invention represents a compound in which a carbonyl group (—C(=O)—) is bonded to two hydrocarbyl groups, and the ketone can be classified into aliphatic ketone, alicyclic ketone, aromatic ketone, saturated ketone and unsaturated ketone according to the different hydrocarbyl group in the molecule, specific examples include, but are not limited to, acetone, acetophenone, methyl isobutyl ketone or methyl pyrrolidone.

The term "ether solvent" used in the present invention represents a chain compound or a cyclic compound having an ether bond —O— and having 1 to 10 carbon atoms, and specific examples include, but are not limited to, tetrahydrofuran, diethyl ether, propylene glycol monomethyl ether, methyl tert-butyl ether or 1,4-dioxane.

The term "alcohol solvent" used in the present invention represents a group derived from substituting one or more hydrogen atoms on "$C_{1-6}$ alkyl" with one or more "hydroxyl groups", the "hydroxyl group" and "$C_{1-6}$ alkyl" are as defined above, and specific examples include, but are not limited to, methanol, ethanol, isopropanol, n-propanol, isopentyl alcohol or trifluoroethanol.

The term "nitrile solvent" used in the present invention represents a group derived from substituting one or more hydrogen atoms on "$C_{1-6}$ alkyl" with one or more "cyano groups", the "cyano group" and "$C_{1-6}$ alkyl" are as defined above, and specific examples include, but are not limited to, acetonitrile or propionitrile.

The term "ester solvent" used in the present invention represents a combination of a lower organic acid having 1 to 4 carbon atoms and a lower alcohol having 1 to 6 carbon atoms, and specific examples include, but are not limited to, ethyl acetate, isopropyl acetate or butyl acetate.

The term "mixed solvent" used in the present invention represents a solvent obtained by mixing one or more different kinds of organic solvents in a certain ratio, or a solvent obtained by mixing an organic solvent with water in a certain ratio; the mixed solvent is preferably a mixed solvent of an alcohol and an ether; the mixed solvent of the alcohol and the ether is preferably a mixed solvent of methanol and diethyl ether, and the ratio is preferably 1:10.

The "X-ray powder diffraction pattern or XRPD" in the present invention means that according to the Bragg formula $2d \sin \theta = n\lambda$ (wherein, $\lambda$ is the wavelength of the X-ray, $\lambda=1.54056$ Å, the order of diffraction n is any positive integer, generally first-order diffraction peak is taken, n=1), when the X-ray is incident at a sweep angle $\theta$ (the angle of incidence angle, also called the Bragg angle) on an atomic plane of a crystal or partial of a crystal sample having a d-matrix plane spacing, the Bragg equation can be satisfied, and the X-ray powder diffraction pattern is measured.

The "differential scanning calorimetry or DSC" used in the present invention refers to the temperature difference and heat flow difference measured between a sample and a reference during temperature rise or constant temperature of the sample to characterize all physical and chemical changes related to thermal effects, and to get the phase change information of the sample.

The "2θ or 2θ angle" used in the present invention refer to diffraction angle, θ is a Bragg angle, and the unit is ° or degree, and the error range of 2θ is ±0.1 to ±0.5, preferably ±0.1 to ±0.3, more preferably ±0.2.

The "plane spacing or interplanar spacing (d value)" used in the present invention represented for the three unit vectors a, b, c selected from space lattice, which are not parallel to each other and which connect two adjacent lattice points, these points divided the lattice into juxtaposed parallelepiped unit, named plane spacing. The spacial lattice is linearly divided according to the determined parallelepiped unit, and a set of linear grids is obtained, which is called a space lattice or lattice. The lattice reflects the periodicity of the crystal structure by geometric points and lines, and the interplanar spacing (i.e, the distance between two adjacent parallel planes) of different lattice plane is different; the unit is Å or Ångström.

The invention further relates to the pharmaceutical composition comprising the compound represented by formula (I), or crystal form I thereof, and optionally one or more pharmaceutically acceptable carriers and/or diluents. The pharmaceutical composition can be formulated into any of the pharmaceutically acceptable dosage forms. For example, the compound represented by formula (I) of the present invention, crystal form I or the pharmaceutic preparation can be formulated into tablets, capsules, pills, granules, solutions, suspensions, syrups, injections (including injections, sterile powder for injection and concentrated solution for injection), suppository, inhalation or spray.

Furthermore, the pharmaceutical composition of the present invention can also be administered to a patient or subject in need of such treatment by any suitable mode of administration, such as oral, parenteral, rectal, pulmonary or topical administration. When used for oral administration, the pharmaceutical composition can be formulated into an oral preparation, such as an oral solid preparation such as tablet, capsule, pill, granule, or the like; or an oral liquid preparation such as oral solution, oral suspension, syrup and the like. When formulated into an oral preparation, the pharmaceutical preparation can further contain suitable filler, binder, disintegrant, lubricant, and the like. When used for parenteral administration, the pharmaceutical preparation can be prepared as an injection preparation, including injection, sterile powder for injection, and concentrated solution for injection. When formulated as an injection preparation, the pharmaceutical composition can be prepared by conventional methods in the existing pharmaceutical field. When the injection preparation is formulated, there may be no additional agent added to the pharmaceutical preparation, or suitable additional agent may be added depending on the nature of the drug. When used for rectal administration, the pharmaceutical preparation can be formulated into a suppository or the like. For pulmonary administration, the pharmaceutical preparation can be formulated as an inhalant or a spray. In certain preferred embodiments, the compound represented by formula (I) of the present invention or crystal form I thereof is present in the pharmaceutical composition or medicament in a therapeutic and/or prophylactically effective amount. In certain preferred embodiments, the compound represented by formula (I) of the present invention or crystal form I thereof is present in the pharmaceutical composition or medicament in unit dosage form.

The compound represented by formula (I) of the present invention and crystal form I thereof can be used for manufacturing a medicament for treating disease related to opioid receptor (MOR) agonist. Accordingly, the present application also relates to the use of the compound represented by formula (I) of the present invention and crystal form I thereof for manufacturing a medicament, said medicament is used for treating opioid receptor (MOR) agonist related diseases. Furthermore, the present application also relates to a method of inhibiting opioid receptor (MOR) agonist related disease, which comprises: administering to a subject in need thereof a therapeutically and/or prophylactically effective amount of the compound represented by formula (I) of the present invention, crystal form I thereof, or the pharmaceutical composition of the present invention.

In certain preferred embodiments, the disease is opioid receptor (MOR) agonist related disease, which is selected from the pains.

Advantageous Effect of the Present Invention

Compared with the prior art, the technical solution of the present invention possesses the following advantages:

Studies have shown that the compound represented by formula (I) prepared by the present invention has excellent solubility;

The crystal form I exhibits higher melting point, better solubility, higher purity, and no crystal form change (detected by XRPD) under high temperature and high humidity conditions; crystal form I of the compound represented by formula (I) obtained by the technical solution of the present invention can meet the medicinal requirements for production, transportation and storage, and the production process is stable, reproducible and controllable, which may be adapted to industrial production.

DETAILED DESCRIPTION OF THE PREFERRED EMBODIMENT

Figure 1:
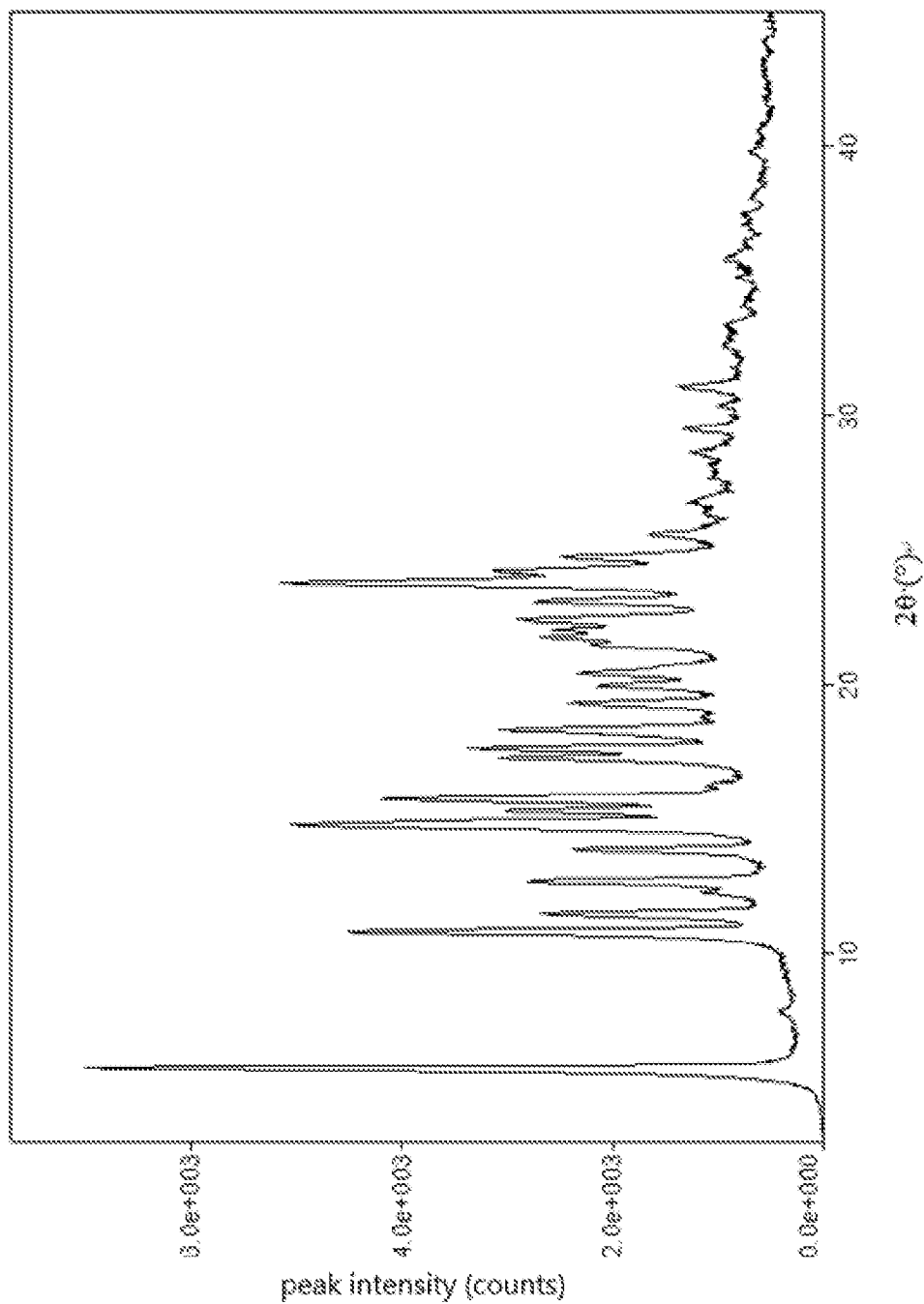
FIG. 1 is an XRPD spectrogram of crystal form I of the compound represented by formula (I).

The present invention is further explained in more detail with the embodiments hereinafter, which are only intended to illustrate the technical solution of the present invention and not to limit the essence and scope of the present invention.

Testing conditions for the instruments used in the experiment:
1. Differential Scanning calorimeter (DSC)
Instrument model: Mettler Toledo DSC3$^+$ STAR$^e$ System
Purge gas: nitrogen (50 mL/min)
Heating rate: 10.0° C./min
Temperature range: 20-250° C.

2. X-ray Powder Diffraction (XRPD)
Instrument model: Rigaku UltimaIV X-ray powder diffractometer
Ray: Monochrome Cu-Kα ray (λ=1.5418 Å)
Scanning method: θ/2θ, scanning range: 3-45°
Voltage: 40 kV
Current: 40 mA
3. Thermogravimetric Analysis (TGA)
Instrument model: Mettler Toledo TGA2 STAR$^e$ System
Purge gas: nitrogen
Heating rate: 10.0° C./min
Temperature range: 20-250° C.

Comparative Experiment 1. Preparation of the (1S, 4S)-4-ethoxy-N-(2-((R)-9-(pyridin-2-yl)-6-oxaspiro[4.5]deca-9-yl)ethyl)-1,2,3,4-tetrahydronaphthalen-1-amine (Compound 19 or Compound Represented by Formula (II))

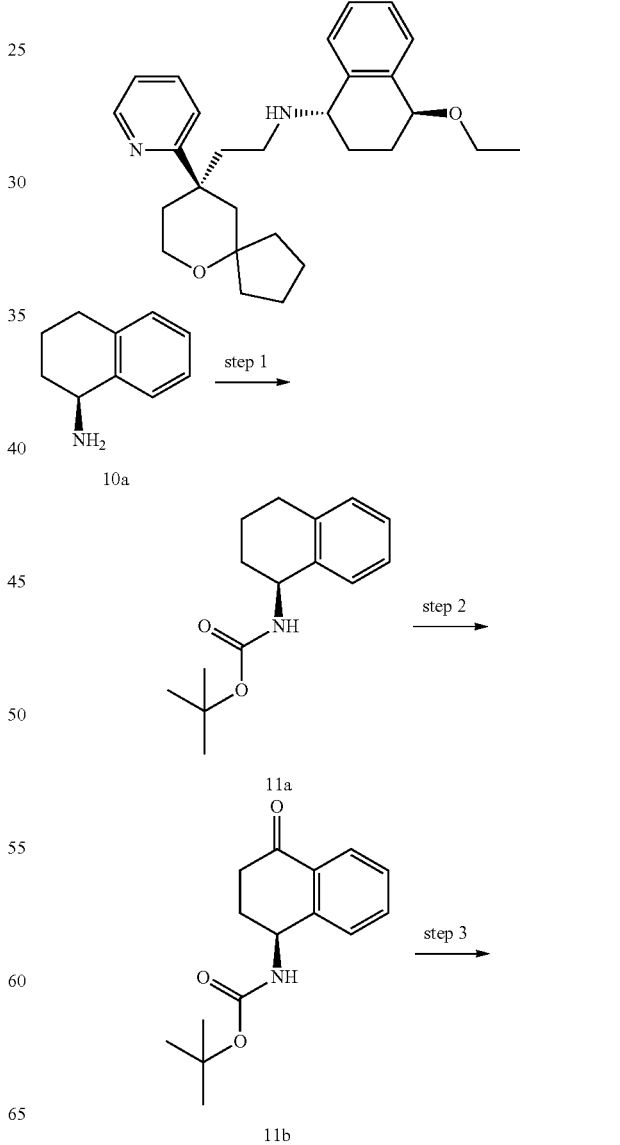

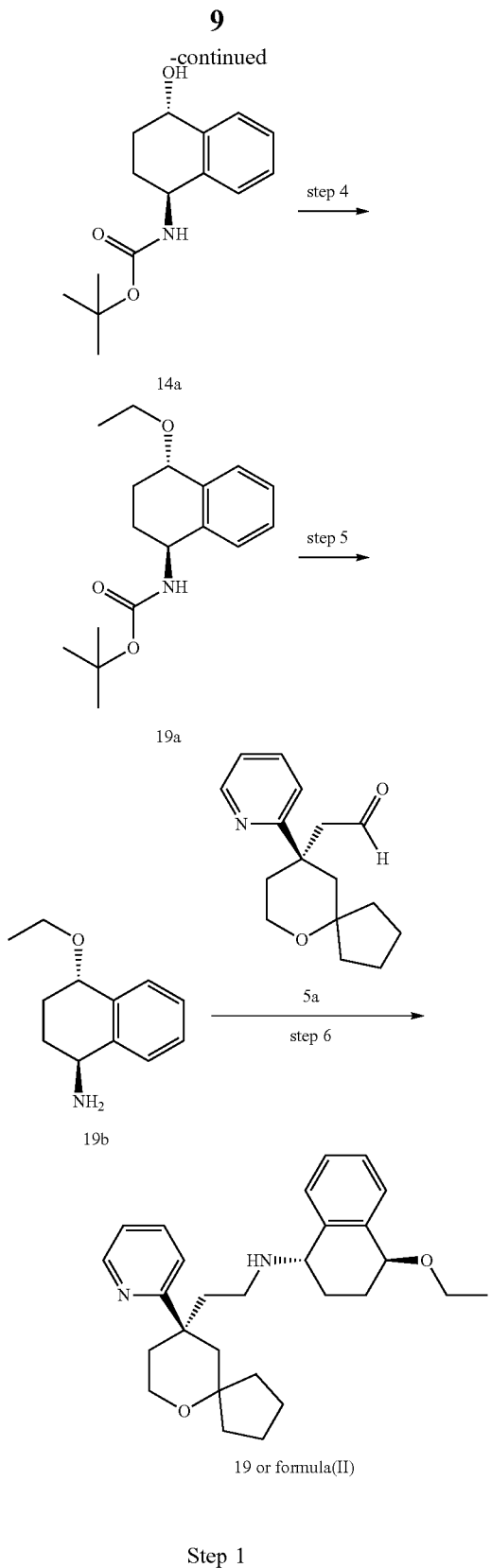

*Chemie-International Edition*, 45(28), 4641-4644, 2006") was dissolved in 100 mL dichloromethane, then triethylamine (5.7 mL, 40.82 mmol) and di-tert-butyl dicarbonate (4.9 g, 22.45 mmol) were added into the solution, and stirred to react for 12 hours. The reaction mixture was washed sequentially by water (100 mL) and saturated bicarbonate solution (100 mL), the organic phase was dried over anhydrous sodium sulfate and then filtered, and the filtrate was concentrated under reduced pressure to deliver the crude product of the title compound 11a (5.6 g, pale yellow oil), which was used directly in the next step without further purification.

MS m/z (ESI): 248.3 [M+1]

Step 2

(S)-Tert-butyl (4-oxo-1,2,3,4-tetrahydronaphthalen-1-yl)carbamate 11b

The crude product of (S)-1,2,3,4-tetrahydronaphthalen-1-tert-butyl carbamate 11a (5.6 g, 20.41 mmol) was dissolved into a 90 mL mixture of acetone and water (V/V=2:1), magnesium sulfate (5.5 g, 45.66 mmol) was added, then potassium permanganate (7.22 g, 45.66 mmol) was slowly added while stirring, and the mixture was stirred to react for 12 hours. The reaction mixture was concentrated under reduced pressure, and the residue was purified by silica gel column chromatography using n-hexane and EtOAc as eluent to give the title product 11b (3.1 g, off-white solid), yield: 52%.

MS m/z (ESI): 262.3 [M+1]

Step 3

(1S,4S)-4-hydroxy-1,2,3,4-tetrahydronaphthalen-1-tert-butyl carbamate 14a (S)-Tert-butyl (4-oxo-1,2,3,4-tetrahydronaphthalen-1-yl)carbamate 11b (100 mg, 0.883 mmol) was dissolved in 5 mL toluene, the temperature was cooled down to 0° C., then (R)-2-methyl-CBS-oxazole borane (0.1 mL, 0.076 mmol) was added and stirred for 5 mins, and then borane methyl sulfide (0.88 mL, 0.76 mmol) was added and stirred to react for 2 hours. 50 mL saturated sodium chloride solution were added to quench the reaction, then extracted with EtOAc (30 mL×3), and the organic phases were combined and washed by saturated sodium chloride solution (30 mL×3), dried over anhydrous sodium sulfate, and filtered. The filtrate was concentrated under reduced pressure, and the residue was purified by thin layer chromatography using dichloromethane and methanol as eluent, to give the title product 14a (60 mg, white solid), yield 60%.

MS m/z (ESI): 208.3 [M−55]

Step 4

(1S,4S)-4-ethoxy-1,2,3,4-tetrahydronaphthalen-1-tert-butyl carbamate 19a

The crude product of (1S)-4-hydroxy-1,2,3,4-tetrahydronaphthalen-1-tert-butyl carbamate 14a (850 mg, 3.23 mmol), silver oxide (76 mg, 0.33 mmol) and ethyl iodide (1.3 mL, 16.15 mmol) were dissolved in dichloromethane (30 mL), and the reaction was stirred for 48 hours and then filtered. The filtrate was concentrated under reduced pressure to deliver the crude product of the title compound 19a

Step 1

(S)-1,2,3,4-tetrahydronaphthalen-1-tert-butyl carbamate 11a (S)-1,2,3,4-tetrahydro-1-naphthylamine 10a (3 g, 20.41 mmol, prepared by the method disclosed in "*Angewandte*

(800 mg, yellow oil), which was used directly in the next step without further purification.

MS m/z (ESI): 236.1 [M−55]

Step 5

(1S,4S)-4-ethoxy-1,2,3,4-tetrahydronaphthalen-1-amine 19b

The crude product of compound 19a (698 mg, 2.4 mmol) was dissolved in 4 mL dichloromethane, 8 mL 4 M hydrogen chloride in 1,4-dioxane was added, and the reaction was stirred for 2 hours. The reaction mixture was concentrated under reduced pressure, triturated in EtOAc (30 mL), and filtered. The filter cake was dissolved in the mixed solution of dichloromethane and methanol (20 mL, V:V=5:1), and the pH of the reaction mixture was adjusted by saturated bicarbonate solution to 7-8. The reaction mixture was concentrated under reduced pressure, washed by the mixed solution (30 mL×2) of dichloromethane and methanol (V:V=5:1), and filtered, and the filtrate was concentrated under reduced pressure to give the crude product of the title compound 19b (310 mg, yellow liquid), which was used directly in the next step without further purification.

MS m/z (ESI): 191.1 [M+1]

Step 6

(1S,4S)-4-ethoxy-N-(2-((R)-9-(pyridin-2-yl)-6-oxaspiro[4.5]decane-9-yl)ethyl)-1,2,3,4-tetrahydronaphthalen-1-amine 19

(R)-2-(9-(pyridin-2-yl)-6-oxaspiro[4.5]decane-9-yl)ethanal 5a (500 mg, 1.85 mmol, prepared by the method disclosed in the Patent Application No. "WO2012129495") and the crude product of the compound 19b (310 mg, 1.85 mmol) were dissolved in dichloroethane (30 mL) and stirred for 40 min, and sodium triacetoxyborohydride (980 mg, 4.63 mmol) was added and the reaction was stirred for 2 hours. The mixture was washed sequentially with saturated bicarbonate solution (30 mL×3) and saturated sodium chloride solution (30 mL×3), the organic phase was dried over anhydrous sodium sulfate, and filtered. The filtrate was concentrated under reduced pressure, and the residue was purified by thin layer chromatography using dichloromethane and methanol as eluent, to give the title product 19 (280 mg, yellow viscous solid), yield: 35%.

Comparative Experiment 2: Purification of (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine (Compound Represented by Formula (II))

The product of comparative experiment 1 (100 mg) was placed in a reaction flask, and then ethanol (0.1 mL) was added. The mixture was heated and refluxed to dissolve, and then cooled down to r.t. to precipitate, filtered, and dried, with a yield of 55%.

Embodiment 1: Preparation of Crystal Form I

Preparation of crystal form I of (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine fumarate salt

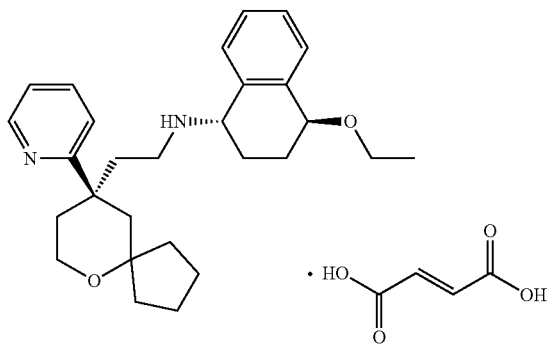

(I)

Figure 2:
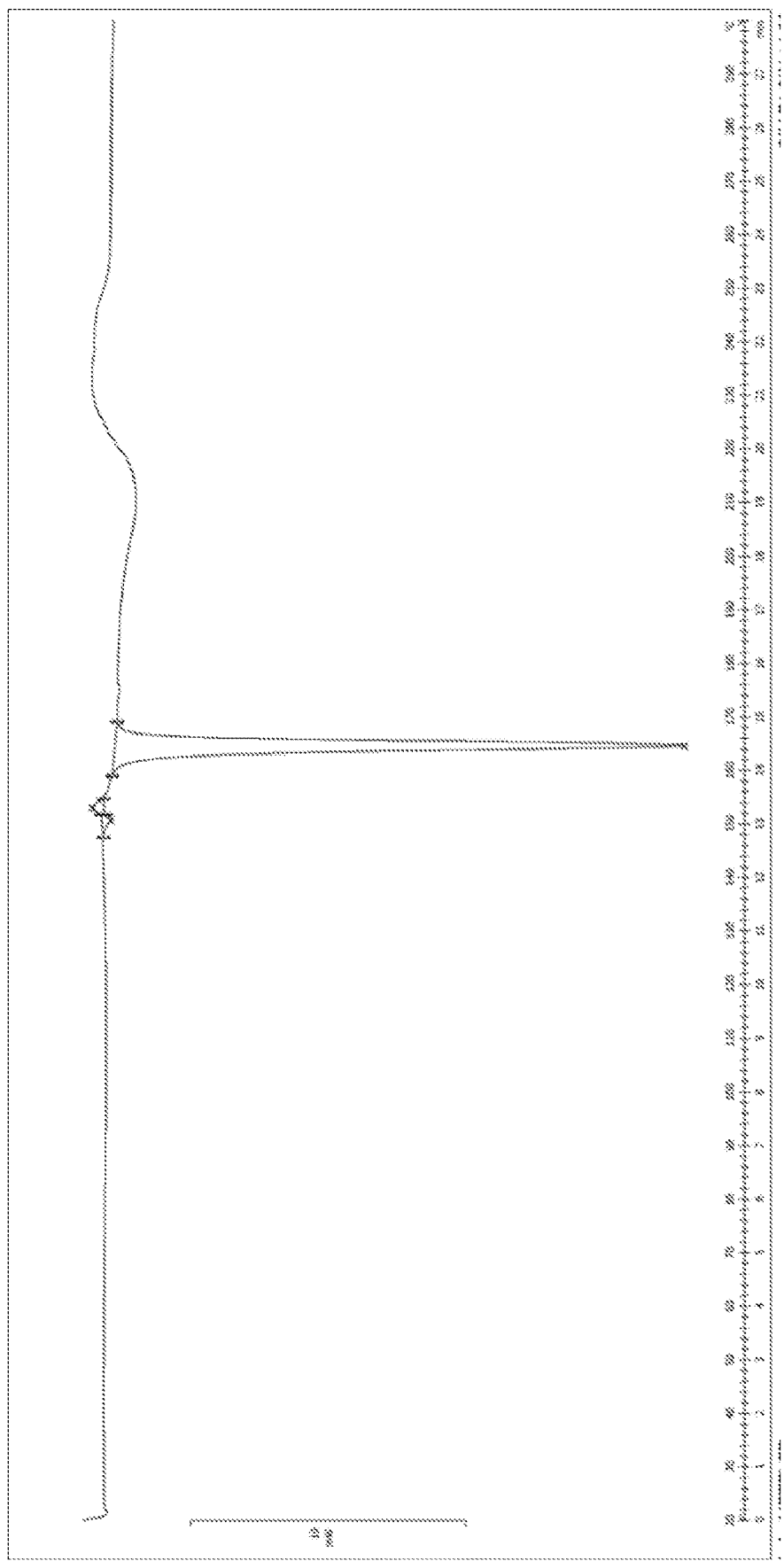
FIG. 2 is a DSC spectrogram of crystal form I of the compound represented by formula (I).

(1S,4S)-4-ethoxy-N-(2-((R)-9-(pyridin-2-yl)-6-oxaspiro[4.5]deca-9-yl)ethyl)-1,2,3,4-tetrahydronaphthalen-1-amine (50 mg, 0.09 mmol) was dissolved in tetrahydrofuran (2.5 mL), and then fumaric acid (23.2 mg, 0.2 mmol) was dissolved in tetrahydrofuran (0.25 mL) and added dropwise into the solution above. The solution was clear after stirring, heated to slightly boiling and stirred to dissolution. Then the solution was cooled down naturally to r.t., and stirred for 16 hours. The reaction mixture was then filtered, and the filter cake was drip washed with EtOAc (1 mL×3) and collected, dried in vacuum to give the solid (25 mg, yield 50%). The XRPD spectrogram of the crystal sample is shown in FIG. 1, and the DSC spectrogram thereof is shown in FIG. 2, with 2 endothermic peaks and 1 exothermic peak, of which detailed data are shown in the table below:

| Enthalpy intergration (mJ) | −4.21 | 4.87 | −275.82 |
|---|---|---|---|
| Normalisation (Jĝ−1) | −1.39 | −1.61 | −90.97 |
| Starting melting point (° C.) | 148.49 | 151.52 | 162.48 |
| Peak value (° C.) | 150.61 | 152.81 | 163.49 |
| Left-side area (%) | 62.60 | 43.05 | 51.55 |
| Right-side area (%) | 37.40 | 56.95 | 48.45 |
| Total area (%) | 100.00 | 99.82 | 100.00 |

It can be seen that the starting point of the maximum endothermic peak is around 162.48° C., with a peak value of about 163.49° C., of which the 2θ characteristic peaks is as shown in the table below:

TABLE 1

Characteristic peaks of crystal form I

| Peaks No. | 2θ[°] | d[Å] |
|---|---|---|
| Peak 1 | 5.76 | 15.33 |
| Peak 2 | 7.86 | 11.23 |

TABLE 1-continued

Characteristic peaks of crystal form I

| Peaks No. | 2θ[°] | d[Å] |
|---|---|---|
| Peak 3 | 10.82 | 8.17 |
| Peak 4 | 11.47 | 7.71 |
| Peak 5 | 12.28 | 7.2 |
| Peak 6 | 12.69 | 6.97 |
| Peak 7 | 13.86 | 6.38 |
| Peak 8 | 14.77 | 5.99 |
| Peak 9 | 15.27 | 5.8 |
| Peak 10 | 15.74 | 5.63 |
| Peak 11 | 16.26 | 5.45 |
| Peak 12 | 17.26 | 5.13 |
| Peak 13 | 17.61 | 5.03 |
| Peak 14 | 18.34 | 4.83 |
| Peak 15 | 19.27 | 4.6 |
| Peak 16 | 19.94 | 4.45 |
| Peak 17 | 20.37 | 4.36 |
| Peak 18 | 21.42 | 4.15 |
| Peak 19 | 21.73 | 4.09 |
| Peak 20 | 22.02 | 4.03 |
| Peak 21 | 22.39 | 3.97 |
| Peak 22 | 23.06 | 3.85 |
| Peak 23 | 23.75 | 3.74 |
| Peak 24 | 24.23 | 3.67 |
| Peak 25 | 24.73 | 3.6 |
| Peak 26 | 25.54 | 3.49 |
| Peak 27 | 26.68 | 3.34 |
| Peak 28 | 28.59 | 3.12 |
| Peak 29 | 29.48 | 3.03 |
| Peak 30 | 31.04 | 2.88 |
| Peak 31 | 32.90 | 2.72 |
| Peak 32 | 35.73 | 2.51, |

Figure 3:
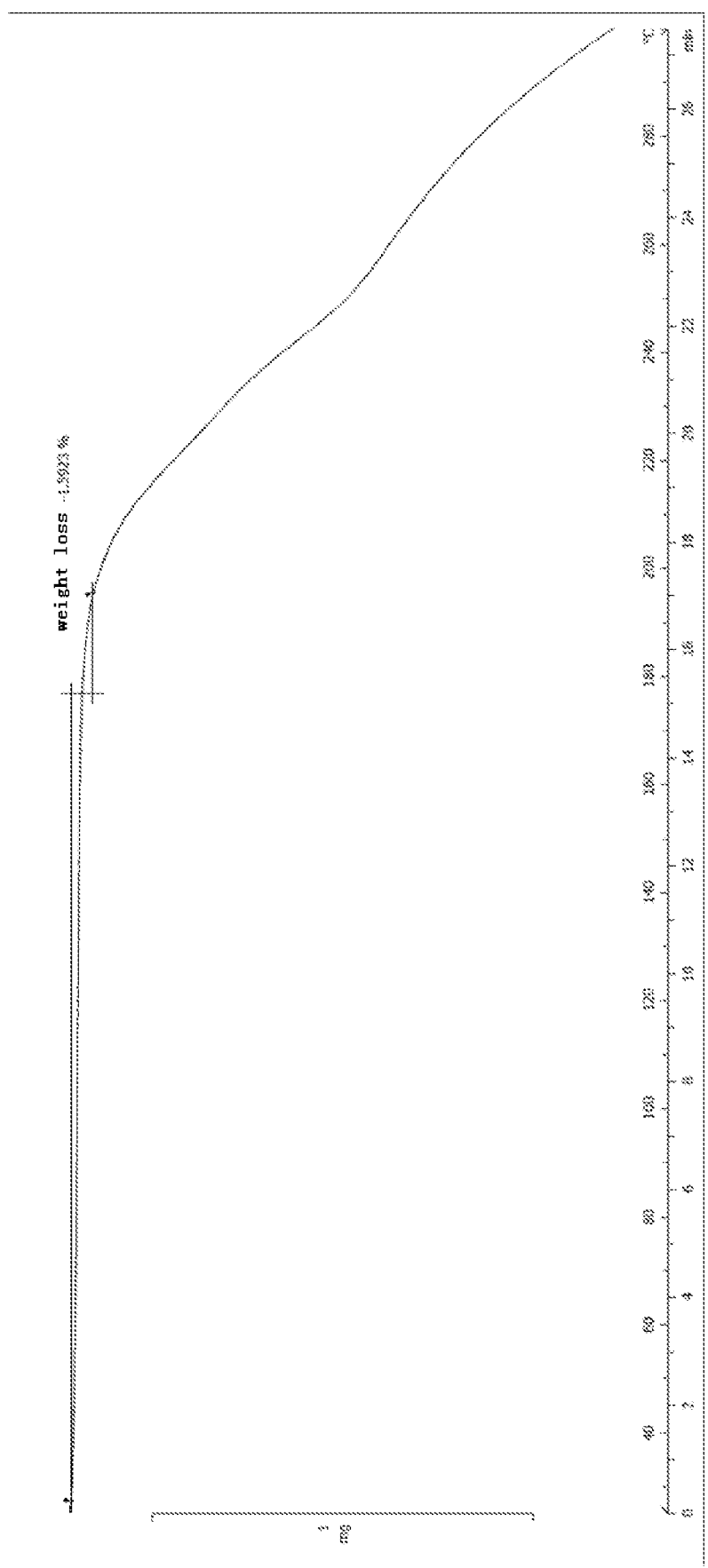
FIG. 3 is a TGA spectrogram of crystal form I of the compound represented by formula (I).

TGA spectrogram is shown in FIG. 3, indicating that crystal form I was an anhydrate;

MS m/z (ESI): 435.5 [M+1]

$^1$H-NMR (400 MHz, DMSO-d$_6$) δ 8.43-8.66 (m, 1H), 7.69-7.80 (m, 1H), 7.42-7.52 (m, 1H), 7.28-7.36 (m, 1H), 7.23 (s, 4H), 6.51 (s, 2H), 4.26-4.35 (m, 1H), 3.85-3.97 (m, 1H), 3.60 (m, 3H), 3.39-3.51 (m, 1H), 2.52-2.61 (m, 1H), 2.30-2.45 (m, 2H), 2.07-2.20 (m, 1H), 1.85-2.07 (m, 3H), 1.20-1.84 (m, 12H), 1.11 (t, 3H), 0.93-1.03 (m, 1H), 0.57-0.72 (m, 1H).

Embodiment 2: Solubility Comparison of the Salt of the Present Invention and Free Base in Water Test sample: compound represented by formula (II) (free base) prepared by comparative experiment 2 and product prepared by embodiment 1 (compound represented by formula (I));

Solvent: pure water;

Experimental Method

The tested sample was weighted and added into pure water, then stirred by a magnetic stirrer overnight, and then filtered and diluted to a certain volume for sample injection;

HPLC chromatographic conditions: acetonitrile-0.1% aqueous trifluoroacetic acid (50:50) used as mobile phase, detection wavelength 264 nm, injection volume 10 μL, flow rate 1.0 mL/min.

Experimental Result

TABLE 2

Solubility comparison of the fumarate salt of the present invention and free base in water

| Sample | Sample weighted (mg) | Solvent volume (mL) | Solubility (mg/mL) |
|---|---|---|---|
| Free base | 21.85 | 0.5 | 0.0022 |
| Compound represented by formula (I) | 47.11 | 1.5 | 31.31 |

Experimental Conclusion

According to the Table 2, the fumarate salt of the present invention has better solubility in water than free base.

Embodiment 3. Stability Investigation of Crystal Form I

The crystal form I sample prepared by embodiment 2 was placed in the dark, sealed and placed flat, and the stability of the sample was investigated long-term (25° C., 60% RH), sampling time was 5 days, and XRPD was used to detect whether the crystal form changed.

Experimental Result

The XRPD peak pattern of crystal form I sample remained unchanged in long-term placement condition (25° C., 60% RH).

Although specific embodiments of the present invention are described above, those skilled in the art should understand that these are only examples for implementation, various modifications and changes may be made to the embodiments without departing from the principle and substance of the present invention. Thus, the scope of the present invention is as defined in the claims attached herein.

What is claimed is:

1. A fumarate salt of the compound represented by formula (II):

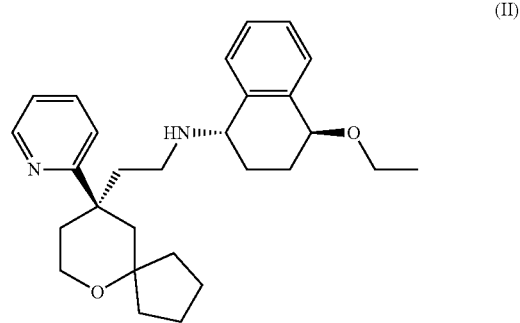 [SMILES: CCO[C@H]1CC[C@H](NCC[C@@]2(c3ccccn3)CCOC3(CCCC3)C2)c2ccccc21]

2. The salt of claim 1, wherein a chemical ratio between the compound represented by formula (II) and fumaric acid is 1:1, and the salt is represented by formula (I):

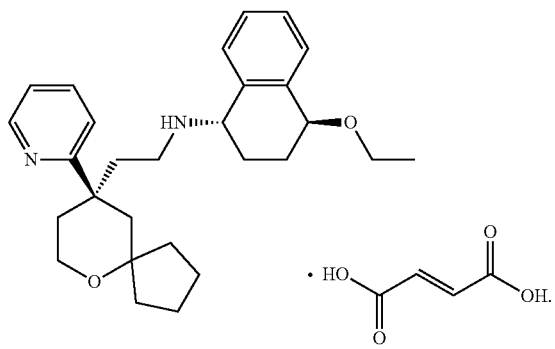 [SMILES: CCO[C@H]1CC[C@H](NCC[C@@]2(c3ccccn3)CCOC3(CCCC3)C2)c2ccccc21 ; O=C(O)/C=C/C(=O)O]

(I)

3. A method for preparing the salt of claim 1, wherein the method comprises reacting (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine with fumaric acid.

4. The method of claim 3, wherein the salt is formed in a solvent, and the solvent is alcohols, ethers or esters, wherein said alcohol solvent is methanol, ethanol or isopropanol, said ether solvent is diethyl ether, methyl tert-butyl ether, tetrahydrofuran or dioxane, and said ester solvent is ethyl acetate, isopropyl acetate or butyl acetate.

5. The method of claim 4, wherein the salt is formed at a temperature of 10-80° C.

6. A pharmaceutical composition comprising the salt of claim 1 and one or more pharmaceutically acceptable carriers, diluents or excipients.

7. A method for treating a disease mediated by an opioid receptor (MOR) agonist in a subject in need thereof, comprising administering an effective amount of the salt of claim 1 to the subject.

8. The method of claim 7, wherein said disease mediated by an MOR receptor agonist is selected from the group consisting of pain, immune dysfunction, inflammation, esophageal reflux, neurological and psychiatric diseases, urinary and reproductive diseases, cardiovascular diseases, and respiratory diseases.

9. The method for preparing the salt of claim 2, comprising reacting (1S,4S)-4-ethoxy-N-(2-((R)-9-(pyridin-2-yl)-6-oxaspiro[4.5]deca-9-yl)ethyl)-1,2,3,4-tetrahydronaphthalen-1-amine with fumaric acid.

10. A method for treating a disease mediated by an opioid receptor (MOR) agonist in a subject in need thereof, comprising administering an effective amount of the pharmaceutical composition of claim 6 to the subject.

11. The method of claim 10, wherein said disease mediated by an MOR receptor agonist is selected from the group consisting of pain, immune dysfunction, inflammation, esophageal reflux, neurological and psychiatric diseases, urinary and reproductive diseases, cardiovascular diseases, and respiratory diseases.

* * * * *